United States Patent [19]

Sharpe-Timms

[11] Patent Number: 5,843,673
[45] Date of Patent: Dec. 1, 1998

[54] METHOD OF SCREENING FOR ENDOMETRIOSIS

[75] Inventor: Kathy Lynn Sharpe-Timms, Columbia, Mo.

[73] Assignee: Curators of the University of Missouri, Columbia, Mo.

[21] Appl. No.: 474,696

[22] Filed: Jun. 7, 1995

Related U.S. Application Data

[63] Continuation-in-part of Ser. No. 328,451, Oct. 25, 1994.
[51] Int. Cl.$^6$ ......................... G01N 33/53; G01N 33/558; G01N 33/68
[52] U.S. Cl. ............................ 435/7.1; 435/7.21; 435/23; 435/806; 436/510; 436/514; 436/65; 436/87; 436/814; 436/906; 128/738; 600/33
[58] Field of Search ..................................... 436/510, 514, 436/65, 87, 814, 906; 435/7.21, 806, 7.1, 25, 7.8; 128/738; 600/33

[56] References Cited

U.S. PATENT DOCUMENTS

| | | |
|---|---|---|
| 3,791,932 | 2/1974 | Schuurs et al. . |
| 3,839,153 | 10/1974 | Schuurs et al. . |
| 3,850,578 | 11/1974 | McConnell . |
| 3,850,752 | 11/1974 | Schuurs et al. . |
| 3,853,987 | 12/1974 | Dreyer . |
| 3,867,517 | 2/1975 | Ling . |
| 3,879,262 | 4/1975 | Schuurs et al. . |
| 3,901,654 | 8/1975 | Gross . |
| 3,935,074 | 1/1976 | Rubenstein et al. . |
| 3,984,533 | 10/1976 | Uzgiris . |
| 3,996,345 | 12/1976 | Ullman et al. . |
| 4,034,074 | 7/1977 | Miles . |
| 4,098,876 | 7/1978 | Piasio et al. . |
| 4,879,219 | 11/1989 | Wands et al. . |
| 5,011,771 | 4/1991 | Bellet et al. . |

OTHER PUBLICATIONS

Hampton et al., Apr. 1994. Expression of messenger ribonucleic acid encoding matrix metalloproteinases and their tissue inhibitors is related to menstruation. J. Endocrinol. 141: R1–R3.

Salamonsen, 1994. Matris metalloproteinases and endometrial remodelling. Cell Biology International 18: 1139–1144.

Hampton et al., Aug. 1995. Tissue inhibitors of metalloproteinases in endometrium of ovariectomized steroid–treated ewes and during the estrous cycle and early pregnancy. Biol. Reprod. 53:302–311.

Lohmander et al., Feb. 1993. Metaloproteinases, tissue inhibitor, and proteoglycan fragments in knee synovial fluid in human osterarthritis. Arthritis and Rheumatism 36: 181–189.

MacLaughlin et al., 1986. Two–dimensional gel electrophoresis of endometrial protein in human uterine fluids: qualitative and quantitative analysis. Biol. Reprod. 34:579–585.

Jellum et al., 1986. High resolution two–dimensional protein electrophoresis in clinical chemistry. Scand. J. Clin. Lab. Investigat. 46(Suppl. 184): 71–76.

Tietz, 1986. Textbook of Clinical Chemistry. W.B. Saunders Company, Philadelphia. p. 560.

Dunselman et al., 1988. The acute–phase response in endometriosis of women. J. Reprod. Fert. 83: 803–808.

Horvat et al., 1993. Two–dimensional electrophoretic analysis of endometrial cellular proteins synthesized during early pregnancy in the mouse. Gynecol. Obstet. Invest. 35: 69–75.

Snipes et al., 1986. Nerve injury stimulates the secretion of apolipoprotein E by nonneuronal cells. Proc. Natl. Acad. Sci. USA 83:1130–1134.

Nothnick et al., Feb. 1994. Detection of a unique 32–kd protein in the peritoneal fluid of women with endometriosis. Fertility and Sterility 61: 288–293.

Clark et al., 1991. Polyclonal and monoclonal antibodies against human tissue inhibitor of metalloproteinases (TIMP) and the design of an enzyme–linked–immunosorbent–assay to measure TIMP. Matrix 11: 76–85 SciSearch Article #FK536.

Bell SC, "Purification of human secretary pregnancy–associated endometrial . . . " *Hum Reprod* 1:313–18 (1986).

Bolen et al., "Reactive and neoplastic serosal tissue". *Am J Surg Path* 10:34–47 (1986).

Catty and Raykundalia, "ELISA and related enzyme immunoassays". In: Catty D (ed) *Antibodies , A Practical Approach*. IRL Press, Oxford. vol. II pp. 97–154.

Cornillie et al., "Expression of endometrial protein PP14 in pelvic and ovarian endometriotic implants" *Hum Reprod* 6:1141–1415 (1991).

Critchley et al., "Role of the ovary in the synthesis of placental protein–14" *J Clin Endocrinol Metab* 75:97–100 (1992).

Haining et al., Epidermal growth factor in human endometrium . . . *Hum Reprod* 6:1200–5 (1991).

Hillam et al., "Local antibody production against the murine toxin of *yersinia pestis* in a golf ball–induced granuloma" *Infect Immun* 10:458–463 (1974).

Hsu et al., "Use of avidin–biotin–peroxidase comples (ABC) in immunoperoxidase techniques: a comparison . . . " *J Histochem Cytochem* 29:577–580 (1981).

Isaacson et al., "Production and secretion of complement component 3 by endometriotic tissue" *J Clin Endocrin Metab* 69:1003–9 (1989).

(List continued on next page.)

*Primary Examiner*—Paula K. Hutzell
*Assistant Examiner*—James L. Grun
*Attorney, Agent, or Firm*—Kohn & Associates

[57] ABSTRACT

A glycoprotein having a molecular weight of 28,000 to 32,000 and an isoelectric point of 7.0 to 9.0, both as determined by two-dimensional SDS polyacrylamide gel electrophoresis, is synthesized and secreted specifically by stromal cells of endometriotic origin. Amino acid residues in the region of the N-terminus of the glycoprotein share amino acid sequence identity with a region of tissue inhibitor of metalloproteinases-1 (TIMP-1). A method of screening for endometriosis is disclosed by detection of lower levels of the protein or TIMP-1 in peritoneal fluid or serum samples of women.

2 Claims, 2 Drawing Sheets

OTHER PUBLICATIONS

Joshi et al., "Serum levels of a progestagen–associated endometrial protein during the menstrual cycle and pregnancy" *J Clin Endo Metab* 55:642–648 (1982).

Joshi et al., "Radioimmunoassay for a progestagen–associated protein of the human endometrium" *J Clin Endo Metab* 52:1185–1192 (1981).

Julkunen et al., "Complete amino acid sequence of human placental protein 14: a progesterone–regulated uterine protein homologus . . . " *Proc. Natl Acad Science USA* 85:8845–49 (1988).

Knudsen KA, "Proteins transferred to nitrocellulose as immunogens" *Anal Biochem* 147: 285–288 (1985).

Kruitwagen et al. "Immunocytochemical marker profile of endometriotic epithelial, endometrial epithelial . . . " *European J Obstet Gynecol Reprod Biol* 41:215–223 (1991).

Lessey et al., "Immunohistochemical analysis of estrogen and progesterone receptors in endometriosis: . . . " *Fertil Steril* 51:409–15 (1989).

Melega et al., "Tissue factors influencing growth and maintenance of endometriosis" *Ann NY Acad Sci.* 622:257–65 (1991).

Osteen et al., "Development of a method to isolate and culture highly purified populations of stromal and epithelial cells . . . " *Fertil Steril* 52:965–72 (1989).

Riittinen, L. "Serous ovarian cyst fludis contain high levels of endometrial placental protein 14" *Tumor Biol* 13:175–9 (1992).

Seppala et al. "Endometrial proteins: A reappraisal" *Hum Reprod* 7:31–8 (1992).

Sharpe et al., "Detection of a progesterone–induced secretory protein synthesized by the uteri . . . " *Fertil Steril* 55:403–10 (1991).

Sharpe et al., "Proliferative and morphogenic changes induced by the coculture of rat uterine and peritoneal cells . . . " *Fertil Steril* 58:1220–9 (1992).

Sharpe et al., "Polypeptides synthesized and released by rat endometriotic tissue differ from those . . . " *Biol Reprod* 48:1334–1340 (1993). (Jun. 1993).

Sharpe et al., "Polypeptides synthesized and released by human endometriosis tissue differ from those of the uterine . . . " *Fertil Steril* 60:839–51 (1993). (Nov. 1993).

Telimaa et al., "Elevated serum levels of endometrial secretory protein PP14 in patients with advanced endometriosis" *Am J Obstet Gynecol* 161:866–71 (1989).

Vernon et al., "Classification of endometriotic implants by morphologic appearance and capacity to synthesize . . . " *Fertil Steril* 801–806 (1986).

Vierikko et al., Steriodial regulation of endometriosis tissue: lack of induction of . . . *Fertil Steril* 43:218–224 (1985).

Weibel ER, "Sterological Methods" In: *Practical Methods for Biological Morphometry,* vol. 1, NY: Acadmic Press, pp. 33–45 (1979).

Sharpe et al., "The synthesis and release of endometriotic secretory proteins differs . . . " Presented at the *48th Ann. Mtg. of The American Fertility Soc.,* New Orleans, Louisiana, (Nov. 2–5, 1992).

Sharpe–Timms et al., "Partial purification and subsequent amino acid sequence analysis of endometriosis protein group–2 (ENDO–2) . . . " (Abstract) Biol. Reprod. 52 (Suppl. 1):73.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (v) FRAGMENT TYPE: N-terminal (xi) SEQUENCE DESCRIPTION: SEQ ID NO:1:

```
Ile Ile Gly Gly Ser Met Asp Ala Lys Gly Ser Phe Pro Cys Gln Ala
1               5                   10                  15
Thr Asn Cys
```

(2) INFORMATION FOR SEQ ID NO:2:

(i) SEQUENCE CHARACTERISTICS:
(A) LENGTH: 25 amino acids
(B) TYPE: amino acid
(C) STRANDEDNESS: single
(D) TOPOLOGY: linear (ii) MOLECULE TYPE: peptide (v) FRAGMENT TYPE: N-terminal (xi) SEQUENCE DESCRIPTION: SEQ ID NO:2:

```
Cys Ser Cys Ala Pro Thr His Pro Gln Thr Ala Phe Cys Asn Ser Asp
1               5                   10                  15
Leu Val Ile Arg Ala Lys Phe Met Gly
            20                  25
```

(2) INFORMATION FOR SEQ ID NO:3:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (v) FRAGMENT TYPE: N-terminal (xi) SEQUENCE DESCRIPTION: SEQ ID NO:3:

```
Ile Ile Gly Gly Ser Met Asp Ala Lys Gly Ser Phe Pro Cys Gln Ala
1               5                   10                  15
Thr Met Cys
```

(2) INFORMATION FOR SEQ ID NO:4:

(i) SEQUENCE CHARACTERISTICS:
(A) LENGTH: 25 amino acids
(B) TYPE: amino acid
(C) STRANDEDNESS: single (D) TOPOLOGY: linear (ii) MOLECULE TYPE: peptide (v) FRAGMENT TYPE: N-terminal (xi) SEQUENCE DESCRIPTION: SEQ ID NO:4:

Asp Ser Val Ala Pro Thr His Pro Gln Thr Ala Phe Cys Asn Ser Asp
1               5                   10                  15
Leu Val Ile Arg Ala Lys Phe Met Gly
            20              25

(2) INFORMATION FOR SEQ ID NO:5:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (v) FRAGMENT TYPE: N-terminal (xi) SEQUENCE DESCRIPTION: SEQ ID NO:5:

Ala Pro Thr His Pro Gln Thr Ala Phe Cys Asn Ser Asp Leu Val Ile
1               5                   10                  15
Arg Ala Lys Phe Met Gly
            20

(2) INFORMATION FOR SEQ ID NO:6:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (v) FRAGMENT TYPE: N-terminal (xi) SEQUENCE DESCRIPTION: SEQ ID NO:6:

Ala Pro Thr His Pro Gln Thr Ala Phe Cys Asn Ser Asp Leu Val Ile
1               5                   10                  15
Arg Ala Lys Phe Met Gly
            20

(2) INFORMATION FOR SEQ ID NO:7:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (v) FRAGMENT TYPE: N-terminal (xi) SEQUENCE DESCRIPTION: SEQ ID NO:7:

Ile Ile Gly Gly Ser Met Asp Ala Lys Gly Ser Phe Pro Cys Gln Ala
1               5                   10                  15

(2) INFORMATION FOR SEQ ID NO:8:

(i) SEQUENCE CHARACTERISTICS:
    (A) LENGTH: 16 amino acids
    (B) TYPE: amino acid

```
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:8:

Ile   Ile   Gly   Gly   Ser   Met   Asp   Ala   Lys   Gly   Ser   Phe   Pro   Trp   Gln   Ala
       1                 5                             10                            15
```

METHOD OF SCREENING FOR ENDOMETRIOSIS

This is a continuation-in-part of application Ser. No. 08/328,451, filed on 25 Oct. 1994, now pending.

GRANT REFERENCE

The research carried out in connection with this invention was supported in part by a grant from the National Institute of Health, DHHS NICHD R29HD29026. The Government has certain rights in this invention.

TECHNICAL FIELD

The present invention relates to the field of fertility and more particularly, to means and methods for determining and diagnosing endometriosis in women.

BACKGROUND OF THE INVENTION

Endometriosis is defined as the ectopic presence of endometrial glands and stroma. Endometriotic tissue is comprised of tissue that is histologically similar yet biochemically and functionally different or out of phase from that of the uterine endometrium.

For example, endometriosis differs from its uterine counterpart in steroid responsiveness and receptor content (Vierikko, et al., 1985; Lessey et al., 1989; Melega et al., 1991) and expression of epidermal growth factor and epidermal growth factor receptor (Melega et al., 1991; Haining et al., 1991). These altered characteristics, combined with an ectopic location, effect the physiological activity of the endometriotic tissue and thereby alter protein synthesis and secretion by the endometriotic tissue. Deviations in protein synthesis and secretion might be useful in developing unique markers for the nonsurgical diagnosis and management of endometriosis. Unfortunately, limited information is available concerning protein synthesis, secretion, regulation and expression in endometriotic tissue.

Applicant has found dissimilarities in protein synthesis and secretory patterns between eutopic and ectopic uterine tissues (endometriotic implants) using a rat model for endometriosis (Sharpe et al., 1991; Sharpe and Vernon, 1993). Three groups of endometriotic proteins, synthesized and released in an alternate fashion from uterine proteins, were identified. Two groups of proteins ($M_r$ 40,000 to 55,000; pI 4.0 to 5.2 and $M_r$ 30,000 to 32,000; pI 7.0 to 9.0) were produced by endometriotic implants and not the uteri. The third protein group, ($M_r$ 70,000; pI 5.7), previously identified in uterine explant cultures as progesterone-induced uterine protein-1 (Sharpe et al., 1991), appeared in endometriotic implant cultures 24–48 hours later than in uterine cultures (Sharpe and Vernon, 1993). The identities, functions, mechanisms of altered protein synthesis and secretion by the ectopic uterine tissues and their correlation to human endometriosis are not known.

Little information in the literature addresses human endometriotic secretory proteins. Isaacson and coworkers (Isaacson et al., 1989) showed that human endometriotic tissues produce and secrete complement component 3 (C3) in an alternate fashion to that of the uterine endometrium. Secretion of C3 into the peritoneal cavity may elicit some of the immunological phenomena observed in patients with endometriosis and be related to the pathophysiology of the disease. However, while C3 may play a role in the pathophysiology of endometriosis, C3 is also produced by other tissues in the body and therefore is not useful in the development of an endometriosis-specific marker for the disease.

Further identification of biochemical dissimilarities between the uterine endometrium and endometriosis in vitro may enhance our understanding of the mechanism(s) of the pathogenicity of the endometriotic tissue in vivo, potentially leading to the development of improved treatment approaches for endometriosis. Therefore, Applicant desired to identify unique proteins synthesized and secreted by human endometriosis and endometrium in vitro and in vivo.

Protein synthesis and secretion by endometrial and endometriotic tissue explants and isolated endometrial and endometriotic epithelial and stromal cells were examined.

Specifically, Applicant has developed by isolation and purification glycoprotein markers indicative of endometriosis thereby eliminating the need for surgical diagnosis of the disease.

SUMMARY OF THE INVENTION AND ADVANTAGES

In accordance with the present invention, there are provided purified and isolated glycoproteins and functional analogs thereof and characterized by:

The first having:
(a) a molecular weight of 35,000 to 55,000 as determined by two-dimensional SDS-PAGE polyacrylamide gel electrophoresis;
(b) having an isoelectric point of 4.0 to 5.5; and
(c) being synthesized and secreted specifically by stromal cells of endometriotic tissue origin.

The second glycoprotein has:
(a) a molecular weight of 28,000 to 32,000 as determined by two-dimensional SDS-PAGE polyacrylamide gel electrophoresis;
(b) an isoelectric point of 7.0 to 9.0; and
(c) synthesized and secreted specifically by stromal cells of endometriotic tissue origin.

The invention further provides a method of diagnosing endometriosis by obtaining endometriosis cell sample from a patient, culturing at least stromal cells from the sample and detecting the presence of the glycoproteins as described above. Alternatively, a body fluid such as peritoneal fluid or serum can be obtained.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 3A–3F are photomicrographs of primary cultures of separated epithelial and stromal cells from endometrial and endometriotic biopsy specimens wherein (FIG. 3A) endometrial epithelial cell culture, day 8, cytokeratin mAb (×400); (FIG. 3B) endometrial epithelial cell culture, day 12, cytokeratin mAb (<open arrow>, three-dimensional mound of epithelial cells; <arrowheads>, interconnecting tubular processes; ×200); (FIG. 3C) endometrial stromal cell culture, day 8, vimentin mAb (×400); (FIG. 3D) endometriotic epithelial cell culture, day 6, BMA 180/cytokeratin mAbs (×200); (FIG. 3E) endometriotic epithelial cell culture, day 8, cytokeratin mAb (×400); (FIG. 3F) endometriotic stromal cell culture, day 8, vimentin mAb (×400).

DETAILED DESCRIPTION OF THE INVENTION

Generally, the present invention provides purified and isolated glycoproteins and functional analogs thereof having specific physical and functional characteristics which characterize the invention over all known prior art.

The glycoproteins are specifically an N-acetyl linked glycoproteins as determined by in vitro incorporation of D-[6-$^3$H]glucosamine and by their binding to wheat germ agglutinin sepharose column (which "sees" certain N-acetylglucosamine and terminal sialic acid residues) (Sharpe et al., 1989, 1991, 1994).

By functional analogs, it is meant that an analog will be generally at least 70% homologous over any portion that is functionally relevant. In more preferred embodiments, the homology will be at least 80% and can approach 95% homology to the glycoprotein. The amino acid sequence of an analog may differ from that of the glycoprotein when at least one residue is deleted, inserted or substituted. Differences in glycosylation can provide analogs. The molecular weight of a glycoprotein can vary between the analog and the present invention due to carbohydrate differences.

Two purified and isolated glycoproteins have been found. The first glycoprotein, presently named ENDO-I (SEQ ID NO: 1), has a molecular weight of 35,000 to 55,000 as determined by two-dimensional SDS-PAGE polyacrylamide gel electrophoresis and an isoelectric point of 4.0 to 5.5. The second glycoprotein isolated, named ENDO-II (SEQ ID No: 2), has a molecular weight of 28,000 to 32,000 and an isoelectric point of 7.0 to 9.0.

Both isolated glycoproteins are secretory proteins which are synthesized and secreted by the diseased endometriosis but not the uterine endometrium in vitro or in vivo.

Applicants have further physically characterized ENDO-I and ENDO-II glycoproteins by determining partial amino acids sequences for the glycoproteins. Specifically, rat and human ENDO-I and ENDO-II were given to the Protein Core Facility at the University of Missouri for amino acid sequencing. Partially purified, wheat germ lectin fractionated ENDO-1 and ENDO-2 proteins from stromal cell culture media were separated by 2D-PAGE and electrophoretically transferred to polyvinylidene difluoride (PVDF) membranes. A minimum of 50 pmol quantities of protein for amino acid sequencing "off blot" is required. Transfer to PVDF membranes overnight at 4° C. provided samples free of contaminants such as Tris, glycine, sodium dodecyl sulfate or acrylamide. Transferred proteins were visualized by Commassie blue staining and cut from the membrane for sequencing.

NH$_2$-terminal sequence analysis was carried out by automated Edman degradation on an Applied Biosystems 470A gas phase sequencer with a Model 120A on-line phenylthiohydantoin analyzer.

The partial amino acids sequences for ENDO-I (SEQ ID No:1) and ENDO-II (SEQ ID No.2) are as follows:

| Partial amino acid sequence for ENDO-1 and ENDO-2 | | |
|---|---|---|
| ENDO-1 | | |
| Primary Sequence SEQ ID NO: 1 | | alternate sequence (SEQ ID NO: 3) |
| 1. | Ile | |
| 2. | Ile | |
| 3. | Gly | |
| 4. | Gly | |
| 5. | Ser | |
| 6. | Met | |
| 7. | Asp | |
| 8. | Ala | |
| 9. | Lys | |
| 10. | Gly | |
| 11. | Ser | |
| 12. | Phe | |
| 13. | Pro | |
| 14. | Cys | |
| 15. | Gln | |
| 16. | Ala | |
| 17. | Thr | |
| 18. | Asn | [Met] |
| 19. | Cys | |
| ENDO-2 | | |
| Primary Sequence SEQ ID NO: 2 | | alternate sequence (SEQ ID NO: 4) |
| 1. | Cys | Asp |
| 2. | Ser | |
| 3. | Cys | Val |
| 4. | Ala | |
| 5. | Pro | |
| 6. | Thr | |
| 7. | His | |
| 8. | Pro | |
| 9. | Gln | |
| 10. | Thr | |
| 11. | Ala | |
| 12. | Phe | |
| 13. | Cys | |
| 14. | Asn | |
| 15. | Ser | |
| 16. | Asp | |
| 17. | Leu | |
| 18. | Val | |
| 19. | Ile | |
| 20. | Arg | |
| 21. | Ala | |
| 22. | Lys | |
| 23. | Phe | |
| 24. | Met | |
| 25. | Gly | |

In the above sequences, the amino acids listed in the alternative in square brackets were found in equal picomolar amounts.

Applicant has further identified ENDO-2 to have sequence homology with TIMP-1 at the N-terminal and ENDO-1 to have sequence homology with haptoglobin-related-gene-product at the N-terminal as shown in Example 3 herein below.

The purified and isolated glycoproteins of the present invention can be isolated by methods known in the art. A specific example of a method is as follows and is also delineated in the experimental section discussed in detail below.

Endometriotic tissues, including red petechia and reddish-brown lesions, were obtained at the time of laparoscopic examination and confirmed by histological evaluation. Endometriotic tissues were classified as proliferative (days 4 to 14) or secretory (days 15 to 28) according to the date of the donor's last menstrual period. Use of medication was also recorded. Additional tissue specimens were transported to the laboratory in saline and dissected free of adnexa.

Endometriotic stromal cells were obtained by enzymatic dissociation and purified by a series of filtrations and sedimentations. Cells were enzymatically dissociated during a one hour incubation in Dulbecco's Modified Eagle's Medium/Ham's F-12 (DMEM/Ham's F-12) containing 0.5% collagenase, 0.02% deoxyribonuclease and 2% horse serum in a shaking incubator at 37° C. After one hour, the solutions containing the dissociated cells were filtered through an 88 $\mu$m nylon mesh filter. The stromal cell fractions that passed through the 88 $\mu$m filter were purified by gravity sedimentation and a final filtration through a 38 $\mu$m nylon mesh to remove epithelial cells. Cell viability (trypan blue exclusion) and number were evaluated.

Cell fractions were diluted to a density of $1 \times 10^6$ viable cells/mL and were plated in plastic organ culture dishes for a total of $8 \times 10^5$ viable cells in a surface area of 176.25 mm$^2$. Cultures were kept in a humidified incubator at 37° C. with 5% $CO_2$. Culture media consisted of DMEM/Ham's F-12 containing 10% heat-inactivated fetal bovine sera for the first six days of culture. By day 8 of culture, the cells had achieved approximately 95% confluence and protein studies were initiated. The media was replaced with serum-free minimal essential medium containing L-[$^{35}$S] methionine (20 $\mu$Ci/mL) for 24 hours. Incubations were terminated by centrifugation of the media at 3000×RPM for 15 minutes at 4° C. Media containing the de novo synthesized proteins were dialyzed (M$_r$ cut off 6–8000) against 1.0 mM tris, pH 8.2 at 4° C. and lyophilized.

As controls for the isolated stromal cell fractions, endometriotic tissue explants (approximately 100 mg wet weight) were incubated in MEM in the presence of L-[$^{35}$S] methionine (20 $\mu$Ci/mL). Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-dimensional polyacrylamide gel electrophoresis (2-D SDS-PAGE) was used to evaluate the de novo synthesized radiolabeled endometriotic proteins. Aliquots of lyophilized cell culture and tissue explant media containing $1.5 \times 10^6$ non-dialyzable cpm (6,000 to 8,000 M$_r$ cutoff) were applied to the first dimension isoelectric focusing gels. Molecular weight markers were added to the polyacrylamide (12%) second dimension slab gels. Proteins separated by two dimensional SDS-PAGE were transferred to nitrocellulose membranes at one amp constant current for one hour and visualized by fluorography. The BioRad™ 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps.

The purified and isolated glycoproteins and functional analogs thereof can be used in a method of diagnosing endometriosis. Generally, a protocol can be used which includes the steps of obtaining either a cell sample or a body fluid sample such as peritoneal fluid sample from a patient during a laparoscopic examination. Peritoneal and ovarian endometriotic tissues including red petechia, reddish-brown lesions, powder burn lesions, white cystic lesions are elevated with biopsy forceps and the area circumscribed by either laser or sharp dissection. Peritoneal fluid is simply aspirated with a syringe from the peritoneal cavity. The date of the patients last menstrual period and use of any medication are also recorded. Endometriotic tissues and fluids are classified as proliferative (days 4 to 14) or secretory (days 15 to 28) according to the date of their last menstrual period. Endometrial dating and the presence of endometriosis is confirmed by histological evaluation of the endometrium. Detection of ENDO-I and ENDO-II would be achieved by means known in the art as described below.

Two-dimensional polyacrylamide gel electrophoresis, as exemplified above and also exemplified in the example section below can be used for identification of the proteins. Other immunoassay methods, such as immunoblot analysis, ELISA radioimmunoassay may also be used. For example, the antibodies may be prepared against a synthetic peptide based on the protein sequence data or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual,* Cold Spring Harbor Laboratory, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982.) The binding of antibodies to a solid support substrate is also well known in the art. (see for a general discussion Harlow & Lane *Antibodies: A Laboratory Manual,* Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, $\beta$-galactosidase, peroxidase, urease, fluorescein, rhodamine, tritium, $^{14}$C and iodination.

These antibodies may then be used to identify ENDO-1 and ENDO-2 by techniques well known to those skilled in the art including radioimmunoassay, ELISA or Western blot analysis (Joshi et al., 1981, 1982; Catty and Raykundalia, 1989; Hsu, 1981). ELISAs are one embodiment of an immunoassay employed to assess the amount of ENDO-1 and ENDO-2 in a specimen. ELISA assays are well known to those skilled in the art. Both polyclonal and monoclonal antibodies can be used in the assays. Where appropriate other immunoassays, such as radioimmunoassays (RIA) or Western Blot can be used as are known to those in the art. Available immunoassays are extensively described in the patent and scientific literature. See, for example, U.S. Pat.

Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; and 5,011,771 as well as Sambrook et al, *Molecular Cloning: A Laboratory Manual,* Cold Springs Harbor, New York, 1992.

The following examples exemplify the isolation, characterization, and use of the glycoproteins of the present invention.

EXAMPLES

Example 1

ISOLATION AND CHARACTERIZATION OF GLYCOPROTEIN

MATERIALS AND METHODS

Endometrial and Endometriotic Tissue

Human tissues were obtained from randomly selected, informed volunteer patients routinely presenting to the physicians in the Department of Obstetrics and Gynecology at the University of Missouri Medical School as approved by the Institutional Review Board. Patients presented for a variety of routine diagnostic and therapeutic examinations including diagnosis of endometrial function, endometriosis, tubal ligation for sterilization, routine gynecological care and gamete intrafallopian transfer.

Endometrial tissue was obtained using a Pipelle™ (Unimar, Wilton, Conn.) endometrial suction curette. Endometriotic tissue was obtained at the time of laparoscopic examination. Peritoneal endometriotic implants, including red petechia and reddish-brown lesions, were elevated with biopsy forceps and the area circumscribed by either laser or sharp dissection. Powder-burn implants and cystic ovarian endometriosis were excluded from the study. Vernon and associates have shown (Vernon et al., 1986) that the metabolic activity of the reddish implants appears to be greatest when compared with the brown or black lesions. Ovarian endometriosis was excluded to eliminate the possibility of "contaminating" ovarian cells in the cell culture experiments. The date of the patients last menstrual period and use of any medication were also recorded. Endometrial and endometriotic tissues were classified as proliferative (days 4 to 14) or secretory (days 15 to 28) according to the date of their last menstrual period. Endometrial dating and the presence of endometriosis were confirmed by histological evaluation by the Pathology Department at the University of Missouri. Tissue specimens were transported to the laboratory in saline and, using a dissecting microscope, dissected free of adnexa. Epithelial and stromal cell cultures plus tissue explant cultures were processed as described below.

Epithelial and Stromal Cell Isolation And Purification

Epithelial and stromal cells were obtained by enzymatic dissociation and a series of filtrations and sedimentations according to the protocol of Osteen et al. (1989) with modifications described by Sharpe et al. (1992). Briefly, cells were enzymatically dissociated from endometrial and endometriotic tissues during an one hour incubation in phenol-red free Dulbecco's Modified Eagle's Medium/Ham's F-12 (DMEM/Ham's F-12; Sigma Chemical Co., St. Louis, Mo.) containing 0.5% collagenase (Clostridium histolyticum, catalogue number 840-7018IH), 0.02% deoxyribonuclease (DNase, Sigma Chemical Co., St. Louis, Mo.) and 2% horse serum (Vector Laboratories, Burlingame, Calif.) in a shaking incubator at 37° C. After one hour, the solutions containing the dissociated cells were filtered through an 88 µm nylon mesh filter. The stromal cell fractions that passed through the 88 µm filter were further purified by gravity sedimentation and a final filtration through a 37 µm nylon mesh to remove remaining epithelial cells. Cell viability (0.04% trypan blue exclusion test) and number (Makler Counting Chamber, T.S. Scientific, Perkasie, Pa.) were evaluated in aliquots of the cells.

The epithelial cell fractions retained by the filters in the initial filtration step were subjected to a second enzymatic digestion for 30 to 45 minutes or until cell clumps were dispersed. The dispersed epithelial cell fractions were further purified by gravity sedimentation and selective attachment procedures (Sharpe et al., 1992). Cell number and viability were evaluated as described for the stromal cell fractions.

Isolation and purification of epithelial and stromal cells yielded an average of $2.1 \times 10^4$ viable epithelial cells and $2.6 \times 10^5$ viable stromal cells per mg of tissue. Both stromal and epithelial cell fractions were diluted to a density of $1 \times 10^6$ viable cells/mL. Stromal cell suspensions (0.8 mL each) were plated in plastic organ culture dishes (Falcon 3037, Falcon Plastics, Oxnard, Calif.) for a total of $8 \times 10^5$ viable cells in a surface area of 176.25 mm$^2$. Epithelial cell suspensions (0.4 mL) were plated in Millicelle CM culture inserts (Millipore, Bedford, Mass.) coated with 0.2 mL of the extracellular matrix Matrigel® (non-diluted; Collaborative Research Inc., Bedford, Mass.) providing a total of $4 \times 10^5$ viable cells in a surface area of 78.50 mm$^2$. Aliquots of the epithelial cell suspensions were also plated on plastic cultureware for immunocytochemical analysis as Matrigel® often created an unacceptable background in the staining process. Other than the elimination of the high background staining, the results of the immunostaining did not vary between the two culture types (matrix vs plastic).

All cultures were kept in a humidified incubator at 37° C. with 5% $CO_2$. Culture media consisted of phenol-red free DMEM/Ham's F-12 containing 10% heat-inactivated fetal bovine sera (GIBCO/BRL, Grand Island, N.Y.) for the first 6 days of culture. By day 8 of culture, the cells had achieved approximately 95% confluence and protein studies were initiated. The cultures were rinsed 3 times with phosphate buffered saline and the media was replaced with serum-free minimal essential medium (MEM; Gibco/BRL, Grand Island, N.Y.) containing L-[$^{35}$S] methionine (20 µCi/mL; Du Pont New England Nuclear, Boston, Mass.) for 24 hours. Incubations were terminated by centrifugation of the media at 3000×RPM for 15 minutes at 4° C. Media containing the de novo synthesized proteins were dialyzed ($M_r$ cut off 6-8000) against 1.0 mM tris (hydroxymethyl) aminomethane HCl, pH 8.2 at 4° C. and lyophilized.

Cell morphology was assessed and photomicrographed at plating (day 0) and days 4, 6, 8 and 12 at ×100, ×200 and ×400 magnification using a Nikon Diaphon™ inverted phase contrast microscope (Nikon, Inc., Garden City, N.Y.) with a Hoffman Modulation Contrast System (Modulation Optics, Inc. Greenvale, N.Y.). Cells were evaluated before and after immunostaining and with a hematoxylin counterstain.

A variety of intermediate filament protein, glycoprotein and secretory protein markers were used to assess the various cell types present in the endometrial and endometriotic cell cultures.

Studies were undertaken to identify a marker which would distinguish between endometriotic cells and peritoneal cells. Murine monoclonal antibodies (MAbs) against: cytokeratins 8, 18 and 19 (for epithelial cells; Biodesign clone NCL-5D3; Kennebunkport, Me.); vimentin (for stromal cells; Boehringer Mannheim clone V9; Indianapolis, Ind.); a human epithelial cell marker directed against a 200 kilo-Dalton glycoprotein, BMA 180 (also known as BW 495/36; for endometrial/endometriotic epithelial cells; Behringwerke AG, Marburg, Germany); and for pregnancy-associated endometrial $\alpha_2$-globulin ($\alpha_2$-PEG; C6H11; for secretory phase endometrial epithelial cells) were used to assess the cells at plating and on days 4, 6, 8 and 12. The $\alpha_2$-PEG (C6H11; 1:100) MAb was used as a marker of secretory phase epithelial cell purification and also as an indicator of physiological function in vitro by Western blot analysis of explant culture media separated by 2D-PAGE.

Single and double labeling immunocytochemical techniques were performed using the Vectastain® ABC (avidin:biotin complex peroxidase procedure) and ABC-AP (avidin:biotin complex alkaline phosphatase procedure) Kits (Vector Laboratories) as per manufacturer's instructions. Peroxidase activity was demonstrated by incubation with 3,3'-diaminobenzidine substrate yielding a brown intracellular precipitate which confirmed peroxidase staining. Alkaline phosphatase activity was demonstrated with the Vectastain® Alkaline Phosphatase Substrate Kit I—Vector Red yielding a pinkish-red stain which confirmed alkaline phosphatase activity. Cells were counterstained with hematoxylin. Cells incubated with phosphate buffered saline substituted in place of primary antibody were included as negative controls in all immunostaining procedures. Using inverted phase contrast microscopy, multiple fields (×200) per cell type were evaluated for the percent of reactive cells.

Tissue Explant Culture

As controls for the isolated epithelial and stromal cell fractions, endometrial and endometriotic tissue explants (approximately 100 mg wet weight) were incubated in MEM in the presence of L-[$^{35}$S] methionine (20 µCi/mL) as previously used by Sharpe et al. (Sharpe et al., 1991) and Sharpe and Vernon (Sharpe and Vernon, 1993). Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-Dimensional Electrophoresis and Western Blot Analysis

Two-dimensional polyacrylamide gel electrophoresis (2-D SDS-PAGE) was performed as previously employed by Sharpe et al. (1993) and Sharpe and Vernon (1993). To evaluate the de novo synthesized radiolabeled proteins, aliquots of lyophilized cell culture and tissue explant media containing 1.5×10$^6$ non-dialyzable cpm (6,000 to 8,000 M$_r$ cutoff) were applied to the first dimension isoelectric focusing gels. Molecular weight markers (Pharmacia LKB Biotechnology, Inc. Piscataway, N.J.) were added to the polyacrylamide (12%) second dimension slab gels. Proteins separated by two dimensional SDS-PAGE were transferred to nitrocellulose membranes (Schleicher and Schuell, Keene, N.H.) at one amp constant current for one hour using the Hoeffer Transphor® Blot System (Hoeffer Scientific, San Francisco, Calif.) and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps. Due to the overload of protein in some of the two-dimensional SDS-PAGE gels and possible loss of resolution following transfer of the proteins to nitrocellulose prior to autoradiography, only protein groups representing at least 10% of the integrated intensity were evaluated. Quantitative comparisons between patients or between tissue/cell cultures were not made.

RESULTS

Endometrial and Endometriotic Tissue Specimens

Twenty-nine specimens were evaluated (Table 1). Twenty-two of the specimens were obtained from women with histories of regular menses. Seven additional specimens were obtained from women with atypical or absent menstrual cycles. Specimens ranged from 29 mg to over 4 g in weight. Up to 100 mg of tissue was used for explant culture and remaining tissue was enzymatically dissociated for the cell culture experiments.

TABLE 1

Source or Tissue Specimens

| Tissue Source | No. of specimens |
|---|---|
| Regular menses | |
| Matched endometrial/endometriosis biopsy | 16 |
| Endometrial biopsy only | 2 |
| Endometriosis biopsy only | 4 |
| Total | 22 |
| Atypical of absent menses | |
| Endometrial biopsy, irregular bleeding | 1 |
| Endometrial biopsy, irregular bleeding-MPA | 1 |
| Endometrial biopsy, perimenopausal | 1 |
| Endometrial biopsy, danazol | 2 |
| Endometrial biopsy, prior hysterectomy | 2 |
| Total | 7 |

Protein Synthesis and Secretion

Figure 1A:
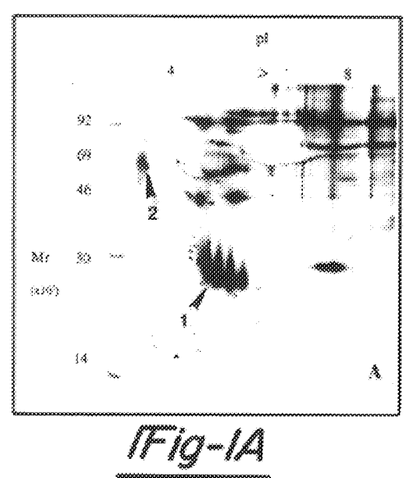
FIGS. 1A–1D are representative two-dimensional SDS-PAGE fluoragraphs of L-[$^{35}$S] methionine-labeled secretory proteins from secretory phase endometrial epithelial cell (FIG. 1A), endometrial stromal cell (FIG. 1B), endometriotic epithelial cell (FIG. 1C), and endometriotic stromal cell (FIG. 1D) culture media.
Figure 1B:
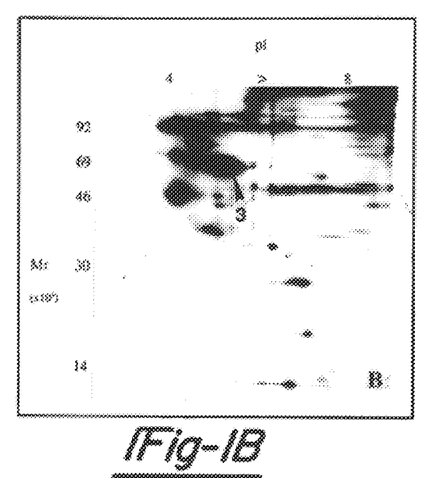
Figure 1C:
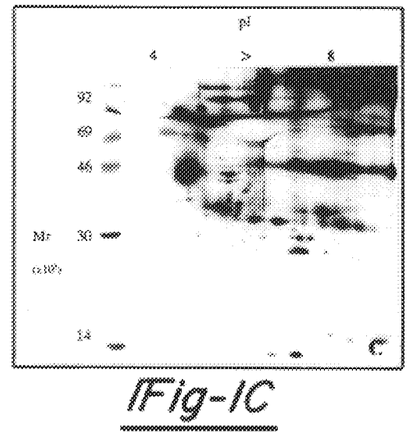
Figure 1D:
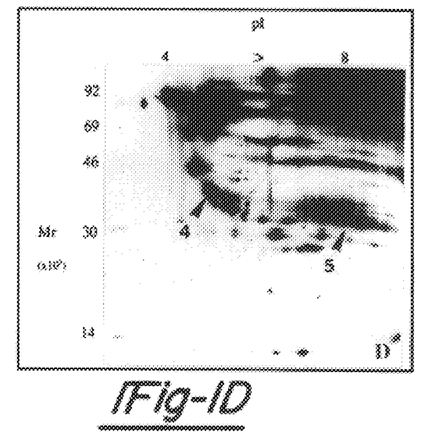

Patterns of proteins synthesis and secretion made from the isolated endometrial and endometriotic epithelial and stromal cell culture media from women with regular menses are shown in FIGS. 1A–1D. Of the hundreds of proteins visualized on the two-dimensional SDS-PAGE fluorographs, five major groups of unique proteins, unique to either endometrial or endometriotic cultures and each representing at least 10% or more of the total integrated intensity of the radioactivity, were resolved and assigned to one of five groups. The proteins assigned to endometrial protein group I (M$_r$ 25,000 to 27,000; pI 4.5 to 5.5) and endometrial protein group II (M$_r$ 68,000 to 72,000; pI 3.0 to 3.2) were synthesized by secretory, but not proliferative phase, endometrial epithelial cells (FIG. 1B). Endometrial protein groups I and II were not found in the culture media of endometrial stromal cells (FIG. 1B), endometriotic epithelial cells (FIG. 1C) or endometriotic stromal cells (FIG. 1D) regardless of the stage of the reproductive cycle. Endometrial protein group III (M$_r$ 70,000; pI 5.7) was synthesized and secreted by secretory, but not proliferative phase, endometrial stromal cells. Endometrial protein group III was also synthesized and secreted by two of seven proliferative endometriotic specimens (not shown) but none of the secretory phase endometriotic specimens tested (FIGS. 1C and 1D). Thus, the proliferative phase release of endometrial protein group III by endometriotic specimens was "out of phase" with that of the secretory phase uterine endometrial release of endometrial protein group III.

Endometriosis protein groups I (M$_r$ 35,000 to 55,000; pI 4.0 to 5.2) and II (M$_r$ 28,000 to 32,000; pI 7.0 to 9.0) were produced by endometriotic stromal cells (FIG. 1B) independent of menstrual cycle stage. Endometriosis protein groups I and II were not synthesized by endometrial epithelial cells (FIG. 1A), endometrial stromal cells (FIG. 1B) or endometriotic epithelial cells (FIG. 1C) regardless of menstrual cycle stage.

Figure 2A:
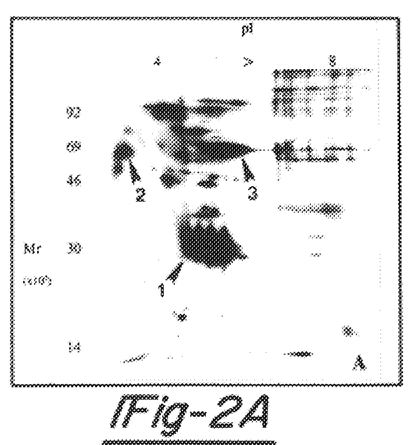
FIGS. 2A–2B are representative two dimensional SDS-PAGE fluoragraphs of L-[$^{35}$S] methionine-labeled secretory proteins from secretory phase endometrial epithelial cell (FIG. 2A), and endometriotic (FIG. 2B) explant culture media.
Figure 2B:
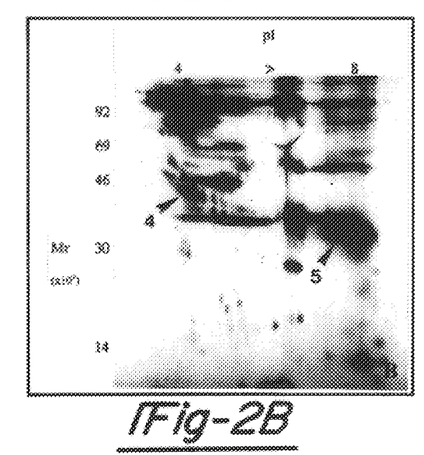

The patterns of synthesis and secretion of the five protein groups visualized and evaluated in the cell culture media were identical to those evaluated in the explant culture media. Endometrial protein groups I, II and III were secretory phase endometrial explant products (FIG. 2A). Endometrial protein groups I and II were not found in endometriotic explant cultures from women with regular menses regardless of the phase of the menstrual cycle (FIG. 2B) while endometrial protein group III was synthesized and secreted by two of seven proliferative phase endometriotic specimens. Also paralleling the cell culture results, endometriosis protein groups I and II were found in endometriotic explant culture media (FIG. 2B) but not endometrial explant culture media (FIG. 2A) regardless of the menstrual cycle stage. Overall, no difference was noted in the pattern of endometrial protein synthesis and secretion between specimens from patients with and without endometriosis.

Western blot analysis of culture media showed that only endometrial protein group I displayed immunoreactivity with the MAb raised against human $\alpha_2$-PEG. No immunoreactivity for $\alpha_2$-PEG was detected in the endometriotic culture media by Western blot analysis. This parallels the lack of $\alpha_2$-PEG immunoreactivity found in the endometriotic epithelial cells as described below.

A limited number of specimens were cultured from women reporting atypical or absent menses. Proliferative endometrium from a patient with irregular uterine bleeding (no current medication) aberrantly synthesized and secreted secretory phase endometrial protein groups II and III and endometriosis protein groups I and II. This was the only case in which endometrial protein groups II and III were produced by a proliferative endometrial specimen and the only case in which the endometriosis protein groups I and II were produced by an endometrial biopsy specimen in this study. Subsequent histological diagnosis revealed adenomyosis.

Proliferative endometrium from a patient taking medroxyprogesterone acetate (MPA) for irregular uterine bleeding more closely resembled that observed for a proliferative endometrium from patients with regular menses. That is, the proliferative endometrium from the MPA patient did not synthesize the secretory phase endometrial protein group II nor the endometriosis protein groups I and II but did, however, aberrantly synthesize and secrete endometrial protein group III, suggesting that this protein group may be modulated by progesterone (P). Secretory endometrium was obtained from a perimenopausal patient. This specimen lacked the ability to produce endometrial protein groups I and II but retained the ability to produce endometrial protein group III. This perimenopausal specimen did not synthesize and secrete endometriosis protein groups I or II.

The pattern of protein synthesis and secretion was also evaluated from endometriotic tissue specimens obtained from patients taking danazol for endometriosis (n=2) and patients who had undergone a prior hysterectomy (n=2). None of these endometriotic specimens produced the endometrial protein groups I, II or III. However, despite the fact that these women had received therapy for endometriosis, half (n=2/4) of these endometriotic specimens continued to synthesize and secrete endometriosis protein groups I and II.

Epithelial and Stromal Cell Culture

Figure 3A:
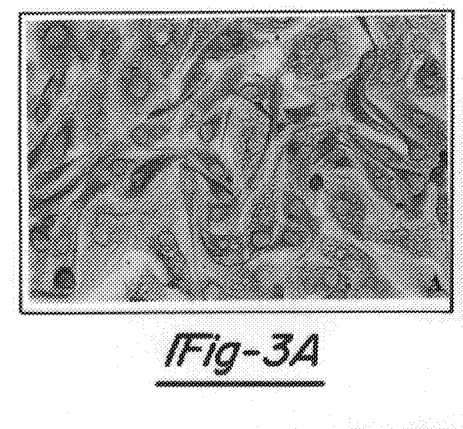
Figure 3B:
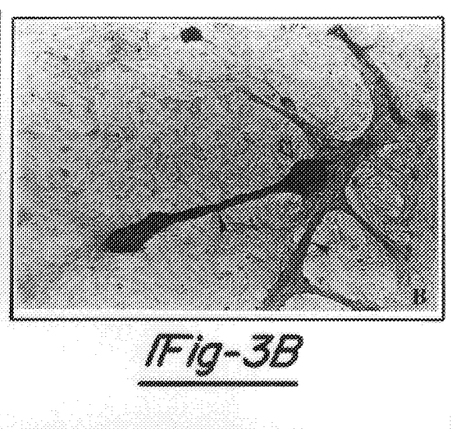
Figure 3C:
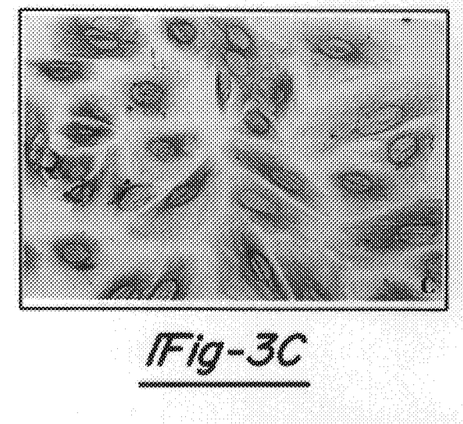

Morphologically, by day 8 of culture, endometrial epithelial cells cultured on the extracellular matrices plated on a semipermeable membrane appeared as homogeneous populations of tadpole-shaped cells with prominent, off-centered nuclei and whorling cell—cell processes that wrapped around adjacent cells (FIG. 3A). By day 12 of culture, the monolayers of endometrial epithelial cells formed three-dimensional mounds of cells which appeared interconnected by tubular processes resembling glandular-like structures (FIG. 3B). Endometrial stromal cells displayed a homologous, cobblestone mosaic-like, single cell monolayer pattern. The endometrial stromal cells had centrally located nuclei, distinct cytoplasmic borders which did not overlap and did not demonstrate cell—cell processes throughout the experiment (FIG. 3C).

Figure 3D:
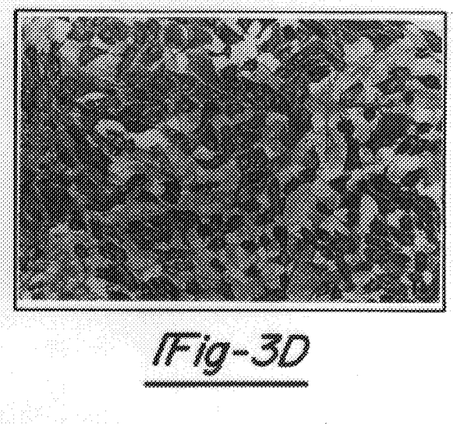
Figure 3E:
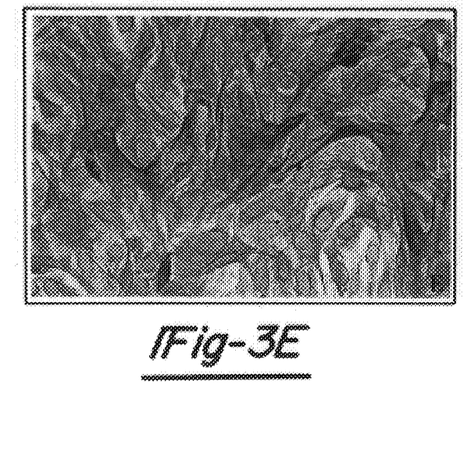
Figure 3F:
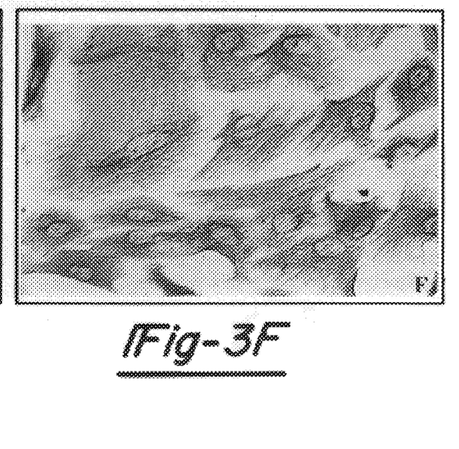

Cell fractions isolated from the endometriotic specimens contained morphologically and immunocytochemically distinct populations of cells. Subconfluent endometriotic epithelial cell fractions observed on days 4 and 6 (FIG. 3E) contained two layers of cells as determined by inverted phase contrast microscopy. An upper layer of cells with multiple long, ultrafine cell—cell processes appeared to be precursors to the tadpole-shaped endometriotic epithelial cells. A sublayer of larger, polymorphous-shaped cells displayed a continuum of cell morphology ranging from polygonal to elongated spindle-like shapes which were not observed in any of the endometrial epithelial cell cultures. By day 8 of culture, the surface layer had overgrown the sublayer so that the cells of the endometriotic epithelial cell cultures (FIG. 3E) appeared tadpole-shaped and morphologically similar to the endometrial epithelial cell cultures (FIG. 3A). The endometriotic stromal cell fractions (FIG. 3F) appeared as single cell monolayers with cells which had centrally located nuclei, distinct cytoplasmic borders and no obvious cell—cell processes much like the morphology of the endometrial stromal cells (FIG. 3C).

The results of the immunocytochemical staining of the cells did not differ between the day of plating and days 4, 6, 8 and 12 and are presented in Table 2. Endometrial epithelial cells, especially those cells involved in formation of the epithelial cell mounds and tubular gland-like structures, displayed strong immunoreactivity with the cytokeratin and BMA 180 MAbs. Few (<3%) of the cells in the endometrial epithelial cells were decorated with the vimentin MAb suggesting limited stromal cell contamination of the epithelial cell cultures. Secretory, but not proliferative phase, endometrial epithelial cells were also decorated with the $\alpha_2$-PEG MAb (C6H11). The surface layer of tadpole-shaped endometriotic epithelial cells displayed similar immunostaining characteristics to the endometrial epithelial cells for cytokeratin, vimentin and BMA 180, but only the endometrial epithelial cells were decorated with the MAb raised against human $\alpha_2$-PEG (Table 2).

The surface and sublayers of the endometriotic epithelial cell cultures displayed different patterns of immunostaining (Table 2). While both layers stained positively for cytokeratin and negatively for $\alpha_2$-PEG, double antibody staining techniques revealed that only the upper layer of tadpole-shaped cells was decorated with the BMA 180 MAb (FIG. 3D) and only the polymorphous sublayer was decorated with vimentin.

Endometrial and endometriotic stromal cells were both decorated with the vimentin MAb and did not display immunoreactivity with the epithelial cell markers BMA 180 and $\alpha_2$-PEG. However, only the endometriotic stromal cells were decorated with the cytokeratin MAb.

Example 1 has identified distinct differences in the synthesis and release of proteins by human endometriosis and uterine endometrium in culture. Unique, endometriosis-specific secretory proteins are of importance in the development of novel diagnostic, prognostic and therapeutic methods for the management of endometriosis, thereby reducing the need for surgical intervention in the diagnosis and treatment of this disease. Furthermore, understanding biochemical dissimilarities between endometrium and endometriosis will enhance our knowledge of the etiology and/or pathophysiology of the endometriotic tissue potentially leading to new treatment approaches for the disease.

As endometriosis protein groups I and II ($M_r$ 35,000 to 55,000; pI 4.0 to 5.2 and $M_r$ 28,000 to 32,000; pI 7.0 to 9.0, respectively) were synthesized and secreted by endometriotic cultures but not endometrial cultures from women with regular menstrual cycles, they are candidates for the development of markers for endometriosis. In addition to their presence in all endometriosis explant culture and endometriosis stromal cell culture media from patients who were not receiving treatment for the disease, endometriosis protein groups I and II were also found in half of the endometriosis cultures derived from women who either had received danazol or had undergone a prior hysterectomy for endometriosis. The continued synthesis and secretion of endometriosis protein groups I and II by endometriotic tissues from women who had undergone these therapies may be one possible explanation for treatment failures. On only one occasion were the endometriosis proteins observed in endometrial culture media. Curiously, this endometrial biopsy was obtained from a women with irregular uterine bleeding who was subsequently diagnosed with adenomyosis. Evaluation of additional numbers of biopsy specimens from patients with irregular menstrual cycles or who have undergone some form of endometriosis therapy are needed.

Endometriosis protein groups I and II have subsequently been named ENDO-1 and ENDO-2, respectively.

Example 1 has also identified three groups of secretory phase endometrial proteins whose synthesis and secretion by endometriosis is absent or altered. Endometrial protein group I ($M_r$ 25,000 to 27,000; pI 4.5 to 5.5) was identified as the secretory phase endometrial protein $\alpha_2$-PEG on the basis of its unique appearance in the secretory phase of the menstrual cycle, by electrophoretic mobility in two-dimensional SDS-PAGE, by Western blot analysis of endometrial culture media and by immunocytochemistry with cell cultures using the MAb C6H11 raised against human $\alpha_2$-PEG (Bell SC, 1986). Using these same criteria, $\alpha_2$-PEG was not detected in the endometriotic explant or endometriotic cell culture media nor by immunostaining of the endometriotic cell cultures regardless of the day of the reproductive cycle at which the specimens were obtained.

In recent years, $\alpha_2$-PEG has received considerable attention, appearing in the literature under various names including progesterone-associated endometrial protein (PEP), placental protein 14 (PP14) and alpha-uterine protein (AUP) (Seppala et al., 1992). Telimaa and coworkers (1989) found elevated serum levels of PP14 in patients with advanced endometriosis and suggested that the endometriotic lesions were contributing to the elevated serum levels of PP14. Cornillie and coworkers (1991) noted that 36% of all endometriotic lesions studied displayed PP14 immunoreactivity yet as few as 6% of the lesions displayed strong PP14 immunostaining. Low levels or the lack of detection of PP14/$\alpha_2$-PEG in endometriotic tissues or culture media, respectively, may be related to methodology. Cornillie and coworkers (1991) evaluated PP 14 expression in paraffin fixed tissues while Applicant evaluated $\alpha_2$-PEG of culture media and cultured cells. Alternatively, tissues or cells may require the addition of P to the culture media prior to the synthesis and secretion of $\alpha_2$-PEG. Yet, the relatively low number of PP14 immunoreactive endometriotic lesions detected in studies (Cornillie et al., 1991) combined with Applicant's lack of detection of $\alpha_2$-PEG in the endometriosis explant or cell culture media or cultured cells also suggests that the elevated serum levels of this protein in patients with endometriosis may be originating from another source. Recent studies have indeed shown that this protein may also be synthesized and secreted by the ovary (Critchley et al., 1992; Riitten L. 1992). However, due to considerable overlap in PP14 measurements in women with and without endometriosis, measurement of PP14 is not predicted to become a diagnostic or prognostic test for endometriosis (Seppala et al., 1992).

Little is known about endometrial protein group II other than the molecular size and isoelectric point as determined by electrophoretic mobility in two-dimensional SDS-PAGE ($M_r$ 68–72,000; pI 3.0–3.2). Endometrial protein group II appears to be unique to secretory phase endometrial explant and epithelial cell cultures and may, as such, be useful as a marker for endometrial function or dysfunctions such as luteal phase defect. Very limited data (n=2) suggests that medroxyprogesterone acetate therapy may also modulate the synthesis and secretion of endometrial protein group II. This observation remains to be confirmed. Thus, both endometrial protein groups I and II may be useful in monitoring therapeutic modalities for progesterone-modulated endometrial function.

Endometrial protein group III ($M_r$ 70,000; pI 5.7) was a major product of secretory, but not proliferative, endometrial explant and stromal cell cultures and is a marker of endometrial receptivity as set forth in Applicant's co-pending applicant, U.S. Ser. No. 328,905, assigned to the same assignee and incorporated herein by reference. Endometrial protein group III was also found in a proliferative phase endometrial explant culture derived from a patient who was taking MPA for irregular uterine bleeding. These observations suggests that endometrial protein group III is P modulated and may play a role in progesterone-dependent uterine function. The synchronous, proliferative phase synthesis and release of endometrial protein group III by the endometriotic lesion as compared to secretory phase uterine production suggests that the endometriotic tissue responds to stimuli in an altered fashion. The release of an endometrial protein by the endometriotic lesion at an inappropriate time of the menstrual cycle might either enhance or be detrimental to normal physiological events. An additional interesting observation is the presence of endometrial protein group III but not endometrial protein groups I and II in the culture media of a secretory phase specimen obtained from a perimenopausal women. The lack of secretion of endometrial protein group I in perimenopausal patients agrees with earlier reports of the lack of PP14 mRNA expression in postmenopausal endometrium (Julkunen et al., 1988). Altered secretory phase synthesis and secretion of endometrial proteins around the time of the menopause requires further investigation.

Endometrial protein group III may be a homologue to rat progesterone-induced uterine protein-1. Similarities including co-migration in two-dimensional SDS-PAGE, synthesis and secretion under conditions of elevated serum P (Sharpe et al., 1991), and synchronous synthesis and secretion by endometriotic tissues (Sharpe and Vernon, 1993) suggest that endometrial protein group III may be the human homologue for the rat progesterone-induced uterine protein-1.

The distinct differences in endometriosis and endometrial protein synthesis and secretion observed add to the growing list of biochemical dissimilarities which exists between these two tissues.

Despite careful attempts of dissection, minimal amounts of peritoneal tissue remained with the endometriotic lesions as they were placed into tissue explant culture or processed for cell culture. This peritoneal tissue may have been the source of the polymorphous cells of the endometriotic epithelial cell cultures. The polymorphous cells observed in this Example and proliferating peritoneal mesothelial and/or subserosal cells (Bolen et al., 1986) display similar morphologies and both co-express vimentin and lower-molecular weight cytokeratins. Furthermore, the lack of $\alpha_2$-PEG and BMA 180 immunoreactivity suggests that the polymorphous cells are not of endometrial origin. Kruitwagen and others (Kruitwagen et al., 1991) have reported that endometriotic epithelial cells but not peritoneal mesothelial cells are immunoreactive with the BMA 180 MAb. The endometriotic stromal cell cultures may also have contained cells of peritoneal origin which co-expressed cytokeratin and vimentin giving the impression that the endometriotic stromal cells expressed cytokeratin. Alternatively, the presence of peritoneal cells may have altered the intermediate filament expression of the endometriotic stromal cells. Subserosal peritoneal cells have been shown to demonstrate striking changes in intermediate filament expression in response to infiltrating tumors (Bolen, et al., 1986). An antibody which distinguishes between endometriotic stromal and peritoneal cells would be useful; an antibody developed for endometrial protein group III might be useful as such a marker. Nonetheless, in this in vitro cell culture model, much like in vivo, endometriotic epithelial and stromal cells juxtapose peritoneal mesothelial and/or subserosal cells which might elicit or contribute to deviations in protein synthesis and secretion.

centrifuged, dialyzed and lyophilized and the proteins separated and visualized by two-dimensional gel electrophoresis and fluorography. Although hundreds of similar proteins were produced by both tissue types, two major groups of proteins, Groups I and II, were found to be unique secretory products of the epithelial cells of the secretory uterine endometrium and were not secreted by the endometriotic tissue regardless of the cycle day. Secretion of Group III was augmented in stromal cells of the uterine cultures as compared to the endometriotic cultures while secretion of group III was augmented in stromal cells of the uterine cultures as compared to the endometriotic cultures while secretion of Group IV was enhanced in the stromal cells of the endometriotic cultures as compared to those of the uteri.

| Group | Mr | pI | Tissue | Cells |
| --- | --- | --- | --- | --- |
| I | 25–27,000 | 4.5–5.5 | Secretory endometrium (d 19–23) | Epithelial |
| II | 72–85,000 | 3.0–3.2 | Secretory endometrium only | Epithelial |
| III | 70,000 | 5.7 | Uterine > Endometriosis | Stromal |
| IV | 30–32,000 | 6.5–8.0 | Endometriosis > Uterine | Stromal |

The two-dimensional electrophoretic mobility and distinctive epithelial cell secretory pattern suggest that Group I is β-lactoglobulin (pregnancy associated endometrial α-globulin, $\alpha_2$-PEG), a major secretory protein of the glandular epithelium of the human endometrium. Group III co-migrates with the rat progesterone-induced uterine protein-1 (PUP-1, also of stromal origin) and may be the human homologue for PUP-1. The highly acid Group II and basic Group IV have not been previously identified. Overall, the altered patterns of protein synthesis and secretion offer additional insight into the biochemical differences which exist between the uterine endometrium and endometriotic lesion.

TABLE 2

Immunocytochemical Staining of Isolated Populations of Endometrial and Endometriotic Epithelial and Stromal Cell Fractions

|  | Epithelial cell fraction | | | Stromal cell fraction | |
| --- | --- | --- | --- | --- | --- |
|  | Endometrial tissue | Endometriotic tissue | | Endometrial tissue | Endometriotic tissue |
|  | Tadpole | Tadpole | Polymorph | Cobblestone | Cobblestone |
| Cytokeratin | +* | + | + | o | + |
| Vimentin | o† | o | + | + | + |
| BMA 180 | + | + | o | o | o |
| $\alpha_2$-PEG | s‡ | o | o | o | o |

*+, Immunoreactivity detected during proliferative and secretory phases of the menstrual cycle.
†o, no immunoreactivity detected in either phase of the menstrual cycle.
‡s, immunoreactivity detected only in secretory phase of the menstrual cycle.

EXAMPLE 2

The Synthesis And Release Of Endometriotic Secretory Proteins Differs From That Of The Uterine Endometrium To access the ability of the endometriotic lesion to synthesize and secrete endometrial proteins, in vitro protein production by uterine endometrium and endometriotic tissues was examined. Matched biopsy specimens of uterine and endometriotic tissues were collected at the time of laparoscopic diagnosis for endometriosis. Menstrual cycle stage (n=5 follicular [cycle day 4–12] and 7 secretory [cycle day 19–27]) and the presence of endometriosis was documented histologically. Tissue explants plus isolated, purified, 90% confluent epithelial and stromal cells were cultured for 24 hours in minimal essential medium containing $^{35}$S-methionine (100 μCi/ml). Tissue and cell culture media containing the de novo synthesized proteins was

EXAMPLE 3

FURTHER IDENTIFICATION OF GLYCOPROTEINS

As shown in Examples 1 and 2, endometriotic tissues synthesize and secrete two distinct protein groups in culture: endometriosis protein group-1 (ENDO-1) and endometriosis protein group-2 (ENDO-2). Applicant characterized ENDO-1 and ENDO-2 by partial purification, amino acid sequence analysis and comparison of the deduced sequences to data bases to determine sequence homology to known proteins.

De novo synthesized ENDO-2 or ENDO-1 were partially purified from rat endometriotic tissue explant culture media using wheat germ lectin sepharose affinity chromatography and two-dimensional SDS-PAGE. The proteins were electrophoretically transferred to polyvinyl difluoride membranes which were stained with Coomassie blue R-250. The stained proteins corresponding to ENDO-2 or ENDO-1 were cut from the membranes for amino acid sequencing. Partial N-terminal amino acid sequence was determined by automated Edman degradation using an Applied Biosystems 470Aa gas phase sequencer with a Model 120A on-line phenylthiohydantoin analyzer.

Sequence analysis of ENDO-2 yielded 25 residues which share 100% sequence homology with tissue inhibitor of metalloproteinases-1 (TIMP-1) mRNA:

| rENDO-2 (SEQ ID NO: 5) | 4 | APTHPQTAFCNSDLVIRAKFMG | 25 |
|---|---|---|---|
| Match | | APTHPQTAFCNSDLVIRAKFMG | |
| rTIMP-1 (SEQ ID NO: 6) | 97 | APTHPQTAFCNSDLVIRAKFMG | 162 |

This data indicates that ENDO-2 and TIMP-1 share sequence homologies. 2D-Western blot analysis using anti-TIMP-1 antibody was used to confirm amino acid sequence data.

Sequence analysis of ENDO-1 yielded 16 residues which share >95% sequence homology with haptoglobin-related (HPR) gene product mRNA:

| rat ENDO-1 (SEQ ID NO: 7) | 1 | IIGGSMDAKGSFPCQA | 16 |
|---|---|---|---|
| Matching Sequence | | IIGGSMDAKGSFP QA | |
| Rat HPR gene product mRNA (SEQ ID NO: 8) | 84 | IIGGSMDAKGSFPWQA | 131 |

EXAMPLE 4

Applicant screened patients presenting with endometrosis for the presence of TIMP-1 and/or HPR gene product associated with endometriosis.

TIMP-1 is a tissue inhibitor of metalloproteinases. Matrix metalloproteinases (MMPs) are a family of enzymes, including collagenase, gelatinase and stromelysin, capable of degrading most components of the extracellular matrix. TIMP's form irreversible inactive complexes with MMPs and thereby regulate MMP activity in the extracellular milieu. MMP's are involved in embryo implantation, ovulation, uterine and mammary gland involution and branching morphogenesis. MMPs have also been implicated in many pathological diseases that involve tissue destruction, tumor invasion and metastasis, however, little information is available about the role of TIMP-1 in these processes. No prior information is available about the role of TIMP-1 in endometriosis. Applicant has found TIMP-1 in endometriotic tissues and found TIMP-1 circulating in body fluids.

Women presenting with endometriosis were screened for the presence of TIMP-1. TIMP-1 was found localized in endometrial lesions more than in normal tissues using immunohistochemical protocols well known to those skilled in the art as described generally in Stites et al., *Basic and Clinical Immunology*, 8th Ed., Appleton & Lange, Norwalk, Conn.

Immunohistochemical staining (Anti-TIMP-1 antibody was purchased from Triple Point Biologicals) found that TIMP-1 levels were elevated in endometrial lesions compared to normal tissue. Further, using an RIA, TIMP-1 levels were decreased in the peritoneal fluid of women with endometriosis. Controls were fertile and infertile women without endometriosis.

| NUMBER OF PATIENTS WITH TIMP-1 IMMUNOSTAINING | | |
|---|---|---|
| | Endometrium[1] | Endometriosis[2] |
| Proliferative | 1/9 | 5/9 |
| Secretory | 4/7[3] | 7/7 |

[1]Endometrial TIMP-1 staining confined to stroma
[2]Endometriosis TIMP-1 staining identified in glands and stroma
[3]Secretory endometrial staining detected in the mid-to late secretory stage but not the early secretory stage.

| INTENSITY OF TIMP-1 IMMUNOSTAINING[1] | | |
|---|---|---|
| | Endometrium | Endometriosis |
| Proliferative | 0 | +/− |
| Secretory | + | +++ |

[1]0 = little to no staining;
+/− = minimal staining;
+ = moderate staining;
+++ = strong staining

| RADIOIMMUNOASSAY RESULTS | | |
|---|---|---|
| Patient's Diagnosis | N | TIMP-1 (ng/ml) Mean + SE |
| Endometriosis | 16 | 587.7 ± 112.8* |
| Fertile control | 6 | 1734.9 ± 848.7* |

*Significant difference by Student's T-test (P < 0.00001).

A hypothesis for the above observations can be made, but it is not to be construed as limiting the present invention to this one mode of action. The data demonstrates production of TIMP-1 by endometriotic tissues. It can be hypothesized that as uterine TIMP-1 is involved in the balance of matrix metalloproteinase regulated tissue remodeling in the endometrium, endometriotic TIMP-1 may play a role in the regulation of peritoneal tissue remodeling, inflammatory reactions and complement activation and thus may be associated with the etiology and pathophysiology of endometriosis. It can be argued that TIMP-1 is synthesized and/or sequestered in the endometriosis lesions in response to the MMP activity resulting in the decrease found in the peritoneal fluid.

Haptoglobin-related gene product has only been shown to be synthesized by fetal liver. It was therefore unexpected to find sequence homology with ENDO-1. Using an in vitro cell culture model, proteins identified by an anti-Haptoglobin-related gene product antibody are found to be secreted from the stroma but not the epithelium of endometriotic tissue. Therefore, it is possible to diagnosis endometriosis by the present of the haptoglobin-related gene product in a body fluid sample such as peritoneal fluid or serum.

The above examples show the identification of two previously unidentified secretory proteins, ENDO-1 and ENDO-2 from human tissue which are synthesized and secreted from the disease endometriosis but not the uterine endometrium in vitro or in vivo. ENDO-1 and ENDO-2 show sequence homology with haptoglobin-related gene product and TIMP-1, respectively. The examples demonstrate the ability of utilizing the identifications of these proteins, at least quantitatively, for an non-invasive diagnostic tool for determining the disease endometriosis. Such diagnosis of endometriosis would not require the otherwise necessary invasive surgical techniques commonly used. Hence, the present invention not only provides a further understanding of endometriosis causes and effects but also leads to a novel diagnostic and potential treatment of approach by eliminating the need for surgical treatment of the disease.

Throughout this application various publications are referenced. Full citations for the publications are listed below. The disclosures of these publication in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

REFERENCES CITED

Bell S C. Purification of human secretory pregnancy-associated endometrial $\alpha_2$-globulin ($\alpha$2-PEG) from cytosol of first trimester pregnancy endometrium. Hum Reprod 1986; 1:313–18.

Bolen J W, Hammar S P, McNutt M A. Reactive and neoplastic serosal tissue. A light-microscopic, ultrastructural and immunocytochemical study. Am J Surg Path 1986; 10:34–47.

Catty D and Raykundalia C. 1989. ELISA and related enzyme immunoassays. In:Catty D (ed) Antibodies, a practical approach. IRL Press, Oxford. Vol II pp97–154.

Cornillie F J, Lauweryns J M, Seppala, Riittinen L, Koninckx P R. Expression of endometrial protein PP14 in pelvic and ovarian endometriotic implants. Hum Reprod 1991; 6:1141–1415.

Critchley H O D, Chard T, Olajide F, Davies M C, Hughes S, Wang H S, et al. Role of the ovary in the synthesis of placental protein-14. J Clin Endocrinol Metab 1992; 75:97–100.

Haining R E B, Cameron I T, Van Papendorp C, Davenport A P, Prentice A, Thomas E J, et al. Epidermal growth factor in human endometrium: proliferative effects in culture and immunocytochemical localization in normal and endometriotic tissues. Hum Reprod 1991; 6:1200–5.

Hillam R P, Tengerdy R P and Brown G L. Local antibody production against the murine toxin of Yersinia pestis in a golf ball-induced granuloma. 1974; Infect Immun 10:458–463.

Hsu S, Raine L and Fanger H. Use of avidin-biotin-peroxidase comples (ABC) in immunoperoxidase techniques: a comparison between ABC and unlabeled antibody (PAP) procedures. J Histochem Cytochem 1981; 29:577–580.

Isaacson K B, Coutifaris C, Garcia C, Lyttle C R. Production and secretion of complement component 3 by endometriotic tissue. J Clin Endocrin Metab 1989; 69:1003–9.

Joshi S G, Bank J F, Henriques E S, Hakrachi A and Matties G. Serum levels of a progestagen-associated endometrial protein during the menstrual cycle and pregnancy. J Clin Endo Metab 1982; 55:642–648.

Joshi S G, Bank J F and Szarowski D H. 1981. Radioimmunoassay for a progestagen-associated protein of the human endometrium. J Clin Endo Metab 52:1185–1192.

Julkunen M, Seppala M, Janne O A. Complete amino acid sequence of human placental protein 14: a progesterone-regulated uterine protein homologus to beta-lactoblobulins. Proc. Natl Acad Science USA 1988; 85:8845–49.

Knudsen K A. Proteins transferred to nitrocellulose as immunogens. 1985; Anal Biochem 147:285–288.

Kruitwagen R F P M, Poels L G, Willemsen W N P, Jap P H K, de Ronde I J Y, Hanselaar T G J M et al. Immunocytochemical marker profile of endometriotic epithelial, endometrial epithelial, and mesothelial cells: a comparative study. European J Obstet Gynecol Reprod Biol 1991; 41:215–223.

Lessey B A, Metzger D A, Haney A F, McCarty K S, Jr. Immunohistochemical analysis of estrogen and progesterone receptors in endometriosis: comparison with normal endometrium during the menstrual cycle and the effect of medical therapy. Fertil Steril 1989; 51:409–15.

Melega C, Balducci M, Bulletti C, Galassi A, Jasonni V M, Flamigni C. Tissue factors influencing growth and maintenance of endometriosis. Ann NY Acad Sci. 1991; 622: 257–65.

Osteen K G, Hill G A, Hargrove J T, Gorstein F. Development of a method to isolate and culture highly purified populations of stromal and epithelial cells from human endometrial biopsy specimens. Fertil Steril 1989; 52:965–72.

Riitten L. Serous ovarian cyst fluids contain high levels of endometrial placental protein 14. Tumor Biol 1992; 13:175–9.

Seppala M, Julkunen M, Riittinen L and Koistinen R. Endometrial proteins: A reappraisal. Hum Reprod 1992; 7:31–8.

Sharpe K L, Bertero M C, Vernon M W. Detection of a progesterone-induced secretory protein synthesized by the uteri but not the endometriotic implants of rats with induced endometriosis. Fertil Steril 1991; 55:403–10.

Sharpe K L, Zimmer R L, Khan R S, Penney L L. Proliferative and morphogenic changes induced by the coculture of rat uterine and peritoneal cells: a cell culture model for endometriosis. Fertil Steril 1992; 58:1220–9.

Sharpe K L, Vernon M W. Polypeptides synthesized and released by rat endometriotic tissue differ from those of the uterine endometrium in culture. Biol Reprod. 1993; 48:1334–1340.

Sharpe K L, Zimmer R L, Griffin W T, Penney L L. Polypeptides synthesized and released by human endometriosis tissue differ from those of the uterine endometrium in cell and tissue explant culture. Fertil Steril 1993; 60:839–51.

Telimaa S, Kauppila A, Ronnberg L, Suikkari A, Seppala M. Elevated serum levels of endometrial secretory protein PP 14 in patients with advanced endometriosis. Am J Obstet Gynecol 1989; 161:866–71.

Vernon M W, Beard J S, Graves K Wilson E A. Classification of endometriotic implants by morphologic appearance and capacity to synthesize prostaglandin F. Fertil Steril 1986:801–806.

Vierikko P, Kauppila A, Ronnberg L, Vihko R. Steroidal regulation of endometriosis tissue: lack of induction of

I claim:

1. A method of screening for endometriosis in a woman patient of reproductive age by:

(a) obtaining a body fluid sample from the patient, the body fluid sample selected from the group consisting of peritoneal fluid and serum; and (b) detecting the presence of a protein at a level below that of normal controls in the sample wherein endometriosis is indicated in the patient, the protein characterized by
        (i) having a molecular weight of 28,000 to 32,000 as determined by two-dimensional SDS-PAGE polyacrylamide gel electrophoresis;
        (ii) having an isoelectric point of 7.0 to 9.0;
        (iii) being synthesized and secreted specifically by stromal cells of endometriotic origin; and
        (iv) having an N-terminal amino acid sequence as set forth in SEQ ID No:2.

2. A method of screening for endometriosis in a woman patient of reproductive age by:

(a) obtaining a body fluid sample from the patient, the body fluid sample selected from the group consisting of peritoneal fluid and serum; and (b) detecting the presence of tissue inhibitor of metalloproteinases-1 (TIMP-1) in the fluid sample at a level below that of normal controls wherein endometriosis is indicated in the patient.

* * * * *